(12) United States Patent
Chittoor et al.

(10) Patent No.: US 10,351,866 B2
(45) Date of Patent: Jul. 16, 2019

(54) PLANT REGULATORY ELEMENTS AND USES THEREOF

(71) Applicant: Monsanto Technology LLC, St. Louis, MO (US)

(72) Inventors: Jaishree M. Chittoor, Wildwood, MO (US); Stanislaw Flasinski, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 37 days.

(21) Appl. No.: 15/602,069

(22) Filed: May 22, 2017

(65) Prior Publication Data

US 2017/0342428 A1  Nov. 30, 2017

Related U.S. Application Data

(60) Provisional application No. 62/340,656, filed on May 24, 2016.

(51) Int. Cl.
*C12N 15/82* (2006.01)
*C12N 15/00* (2006.01)

(52) U.S. Cl.
CPC .......... *C12N 15/8216* (2013.01); *C12N 15/00* (2013.01); *C12N 2800/00* (2013.01)

(58) Field of Classification Search
None
See application file for complete search history.

(56) References Cited

U.S. PATENT DOCUMENTS

| | | | | |
|---|---|---|---|---|
| 5,352,605 | A * | 10/1994 | Fraley | C07K 14/61 435/320.1 |
| 5,489,520 | A * | 2/1996 | Adams | A01H 4/00 536/23.7 |
| 5,500,365 | A * | 3/1996 | Fischhoff | C07K 14/005 435/418 |
| 6,528,701 | B1 | 3/2003 | Wang et al. | |
| 7,485,461 | B2 | 2/2009 | Hammer | |
| 8,168,859 | B2 | 5/2012 | Abbitt | |
| 9,650,640 | B2 | 5/2017 | Kumar et al. | |
| 9,845,477 | B2 | 12/2017 | Flasinski et al. | |
| 2003/0027312 | A1 | 2/2003 | Derose et al. | |
| 2007/0204367 | A1* | 8/2007 | Flasinski | C12N 15/8216 800/278 |
| 2008/0250529 | A1 | 10/2008 | Sekar et al. | |

FOREIGN PATENT DOCUMENTS

| WO | WO 1992/017580 | | 10/1992 |
|---|---|---|---|
| WO | WO 01/44457 | * | 6/2001 |
| WO | WO 2016/022376 | | 2/2016 |

OTHER PUBLICATIONS

Donald & Cashmore, EMBO J 9:1717-26 (1990).*
Kim et al., Plant Mol Biol 24:105-17 (1994).*
Dolferus et al., Plant Physiol 105:1075-87 (1994).*
Potenza et al., In Vitro Cell Dev Biol Plant 40:1-22 (2004).*
Saha et al., In Silica Biol 7(1 ):7-19 (2007).*
Rose, Curr Top Microbial Immunol, 326:277-90 (2008).*
Bulger & Groudine, Cell 144:327-39, 328 (2011).*
Odell et al., Nature 313:810-12 (1985).*
Benfey et al., "The CaMV 35S enhancer contains at least two domains which can confer different developmental and tissue-specific expression patterns," *EMBO J* 8(8):2195-2202, 1989.
Benfey et al., "The cauliflower mosaic virus 35S promoter: combinatorial regulation of transcription in plants," *Science* 250(4983):959-966, 1990.
Cho et al., "Regulation of root hair initiation and expansin gene expression in *Arabidopsis*," *Plant Cell* 14(12):3237-3253, 2002.
Donald et al., "Mutation of either G box or I box sequences profoundly affects expression from the *Arabidopsis* rbcS-1A promoter," *EMBO J* 9(6):1717-1726, 1990.
International Search Report and Written Opinion for International Application No. PCT/US2017/033832 dated Aug. 17, 2017.
Kim et al., "A 20 nucleotide upstream element is essential for the nopaline synthase (nos) promoter activity," *Plant Mol Biol* 24(1):105-117, 1994.
Mandel et al., "Definition of constitutive gene expression in plants: the translation initiation factor 4A gene as a model," *Plant Mol Biol* 29(5):995-1004, 1995.
Odell et al., "Identification of DNA sequences required for activity of the cauliflower mosaic virus 35S promoter," *Nature* 313(6005):810-812, 1985.
Piechulla et al., "Identification of tomato Lhc promoter regions necessary for circadian expression," *Plant Mol Biol* 38(4):655-662, 1998.
Safrany et al., "Identification of a novel cis-regulatory element for UV-B-induced transcription in *Arabidopsis*," *Plant J* 54(3):402-414, 2008.
Welsch et al., "Structural and functional characterization of the phytoene synthase promoter from *Arabidopsis thaliana*," *Planta* 216(3):523-534, 2003.
Cornejo et al., "Activity of a maize ubiquitin promoter in transgenic rice," *Plant Mol Biol* 23:567-581, 1993.
Wei et al., "Comparative expression analysis of two sugarcane polyubiquitin promoters and flanking sequences in transgenic plants," *J. Plant Physiology* 160:1241-1251, 2003.
Joung et al., "Expression of a polyubiquitin promoter isolated from *Gladiolus*," *Plant Cell Rep* 25:1081-1088, 2006.
Lu et al., "Activity of the 5' regulatory regions of the rice polyubiquitin rubi3 gene in transgenic rice plants as analyzed by both GUS and GFP reporter genes," *Plant Cell Rep* 27:1587-1600, 2008.
Wang et al., "Rice ubiquitin promoters: deletion analysis and potential usefulness in plant transformation systems," *Plant Cell Rep* 22:129-134, 2003.
Holtorf et al., "Comparison of different constitutive and inducible promoters for the overexpression of transgenes in *Arabidopsis thaliana*," *Plant Mol Biol* 29:637-646, 1995.

* cited by examiner

*Primary Examiner* — Russell T Boggs
(74) *Attorney, Agent, or Firm* — Dentons US LLP; Carine Marie Doyle, Esq.

(57) ABSTRACT

The invention provides recombinant DNA molecules and constructs, as well as their nucleotide sequences, useful for modulating gene expression in plants. The invention also provides transgenic plants, plant cells, plant parts, and seeds comprising the recombinant DNA molecules operably linked to heterologous transcribable DNA molecules, as are methods of their use.

20 Claims, No Drawings
Specification includes a Sequence Listing.

PLANT REGULATORY ELEMENTS AND USES THEREOF

REFERENCE TO RELATED APPLICATION

This application claims the benefit of U.S. provisional application No. 62/340,656, filed May 24, 2016, which is herein incorporated by reference in its entirety.

INCORPORATION OF SEQUENCE LISTING

The sequence listing that is contained in the file named "MONS419US_sequence_listing.txt", which is 14.2 KB (as measured in Microsoft Windows®) and was created on May 12, 2017, is filed herewith by electronic submission and is incorporated by reference herein.

FIELD OF THE INVENTION

The invention relates to the fields of plant molecular biology and plant genetic engineering. More specifically, the invention relates to DNA molecules useful for modulating gene expression in plants.

BACKGROUND

Regulatory elements are genetic elements that regulate gene activity by modulating the transcription of an operably linked transcribable DNA molecule. Such elements may include promoters, leaders, introns, and 3' untranslated regions and are useful in the fields of plant molecular biology and plant genetic engineering.

SUMMARY OF THE INVENTION

The invention provides novel gene regulatory elements for use in plants. The invention also provides DNA constructs comprising the regulatory elements. The present invention also provides transgenic plant cells, plants, and seeds comprising the regulatory elements. In one embodiment, the regulatory elements are operably linked to a transcribable DNA molecule. In certain embodiments, the transcribable DNA molecule may be heterologous with respect to the regulatory sequence. Thus, a regulatory element sequence provided by the invention may, in particular embodiments, be defined as operably linked to a heterologous transcribable DNA molecule. The present invention also provides methods of making and using the regulatory elements, the DNA constructs comprising the regulatory elements, and the transgenic plant cells, plants, and seeds comprising the regulatory elements operably linked to a transcribable DNA molecule.

Thus, in one aspect, the invention provides a recombinant DNA molecule comprising a DNA sequence selected from the group consisting of: (a) a sequence with at least about 85 percent sequence identity to any of SEQ ID NOs:1-5 or 7; (b) a sequence comprising any of SEQ ID NOs:1-5 or 7; and (c) a fragment of any of SEQ ID NOs:1-5 or 7, wherein the fragment has gene-regulatory activity; wherein the sequence is operably linked to a heterologous transcribable DNA molecule. By "heterologous transcribable DNA molecule," it is meant that the transcribable DNA molecule is heterologous with respect to the polynucleotide sequence to which it is operably linked. In specific embodiments, the recombinant DNA molecule comprises a DNA sequence having at least about 90 percent, at least 91 percent, at least 92 percent, at least 93 percent, at least 94 percent, at least 95 percent, at least 96 percent, at least 97 percent, at least 98 percent, or at least 99 percent sequence identity to the DNA sequence of any of SEQ ID NOs:1-5. In particular embodiments, the DNA sequence comprises a regulatory element. In some embodiments the regulatory element comprises a promoter. In still other embodiments, the heterologous transcribable DNA molecule comprises a gene of agronomic interest, such as a gene capable of providing herbicide resistance in plants, or a gene capable of providing plant pest resistance in plants. In still other embodiments, the invention provides a construct comprising a recombinant DNA molecule as provided herein.

In another aspect, provided herein are transgenic plant cells comprising a recombinant DNA molecule comprising a DNA sequence selected from the group consisting of: (a) a sequence with at least about 85 percent sequence identity to any of SEQ ID NOs:1-5 or 7; (b) a sequence comprising any of SEQ ID NOs:1-5 or 7; and (c) a fragment of any of SEQ ID NOs:1-5 or 7, wherein the fragment has gene-regulatory activity; wherein the DNA sequence is operably linked to a heterologous transcribable DNA molecule. In certain embodiments, the transgenic plant cell is a monocotyledonous plant cell. In other embodiments, the transgenic plant cell is a monocotyledonous plant cell or a dicotyledonous plant cell.

In still yet another aspect, further provided herein is a transgenic plant, or part thereof, comprising a recombinant DNA molecule comprising a DNA sequence selected from the group consisting of: a) a sequence with at least 85 percent sequence identity to any of SEQ ID NOs:1-5 or 7; b) a sequence comprising any of SEQ ID NOs:1-5 or 7; and c) a fragment of any of SEQ ID NOs:1-5 or 7, wherein the fragment has gene-regulatory activity; wherein the sequence is operably linked to a heterologous transcribable DNA molecule. In specific embodiments, the transgenic plant is a progeny plant of any generation that comprises the recombinant DNA molecule. A transgenic seed comprising the recombinant DNA molecule that produces such a transgenic plant when grown is also provided herein.

In another aspect, the invention provides a method of producing a commodity product comprising obtaining a transgenic plant or part thereof containing a recombinant DNA molecule of the invention and producing the commodity product therefrom. In one embodiment, the commodity product is processed seeds, grains, plant parts, oils and meal.

In still yet another aspect, the invention provides a method of producing a transgenic plant comprising a recombinant DNA molecule of the invention comprising transforming a plant cell with the recombinant DNA molecule of the invention to produce a transformed plant cell and regenerating a transgenic plant from the transformed plant cell.

In certain aspects, the invention provides methods of producing a transgenic plant cell comprising introducing a recombinant DNA molecule provided herein into a plant cell. In certain embodiments, introducing said recombinant DNA molecule into said plant cell comprises transformation, or regenerating a transgenic plant from said plant cell. In further embodiments, introducing said recombinant DNA molecule into said plant cell comprises crossing a transgenic plant provided herein with another plant to produce a progeny plant comprising said plant cell.

In a further aspect, the invention provides methods of producing a transgenic plant comprising transforming a plant cell with a recombinant DNA molecule provided herein. In certain embodiments, methods of the invention further comprise regenerating a transgenic plant from a plant cell transformed with a DNA molecule provided herein.

BRIEF DESCRIPTION OF THE SEQUENCES

SEQ ID NO:1 is a DNA sequence of a regulatory expression elements group (EXP) comprising a promoter derived from a putative ubquitin gene from Blue Grama grass (*Bouteloua gracilis*) operably linked 5' to its native leader which is operably linked 5' to its native first intron.

SEQ ID NO:2 is a promoter sequence derived from a putative ubquitin gene from Blue Grama grass (*Bouteloua gracilis*).

SEQ ID NO:3 is a leader sequence derived from a putative ubquitin gene from Blue Grama grass (*Bouteloua gracilis*).

SEQ ID NO:4 is an intron sequence derived from a putative ubquitin gene from Blue Grama grass (*Bouteloua gracilis*).

SEQ ID NO:5 is a 3' untranslated region (UTR) derived from a putative ubquitin gene from Blue Grama grass (*Bouteloua gracilis*).

SEQ ID NO:6 is a synthetic coding sequence encoding β-glucuronidase designed for expression in a plant cell.

SEQ ID NO:7 is an enhancer derived from the *Bouteloua gracilis* putative ubquitin gene promoter.

SEQ ID NO:8 is a 3' untranslated region (UTR) derived from an *Oryza sativa* Lipid Transfer Protein-like gene (LTP).

SEQ ID NO:9 is an enhanced promoter and native leader sequence derived from Cauliflower mosaic virus.

SEQ ID NO:10 is a 3' untranslated region (UTR) derived from the nopaline synthase gene of *Agrobacterium tumefaciens*.

DETAILED DESCRIPTION OF THE INVENTION

The invention provides DNA molecules having gene-regulatory activity in plants. The nucleotide sequences of these DNA molecules are provided as SEQ ID NOs:1-5 or 7. These DNA molecules are capable of affecting the expression of an operably linked transcribable DNA molecule in plant tissues, and therefore regulating gene expression of an operably linked transgene in transgenic plants. The invention also provides methods of modifying, producing, and using the same. The invention also provides compositions that include transgenic plant cells, plants, plant parts, and seeds containing the recombinant DNA molecules of the invention, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e., a polymer of deoxyribonucleotide bases or a DNA molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation or gene editing.

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As used herein, the term "sequence identity" refers to the extent to which two optimally aligned polynucleotide sequences or two optimally aligned polypeptide sequences are identical. An optimal sequence alignment is created by manually aligning two sequences, e.g., a reference sequence and another sequence, to maximize the number of nucleotide matches in the sequence alignment with appropriate internal nucleotide insertions, deletions, or gaps. As used herein, the term "reference sequence" refers to a DNA sequence provided as SEQ ID NOs:1-5 or 7.

As used herein, the term "percent sequence identity" or "percent identity" or "% identity" is the identity fraction multiplied by 100. The "identity fraction" for a sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a sequence that, when optimally aligned to a reference sequence, provided herein as SEQ ID NOs:1-5 and 7, has at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence. In certain embodiments, provided herein are sequences having a percent identity to any one of SEQ ID NOs: 1-5 or 7, and having the activity of the full length sequence.

Regulatory Elements

Regulatory elements such as promoters, leaders (also known as 5' UTRs), enhancers, introns, and transcription termination regions (also known as 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are therefore useful for modifying plant phenotypes through genetic engineering.

As used herein, a "regulatory expression element group" or "EXP" sequence may refer to a group of operably linked regulatory elements, such as enhancers, promoters, leaders, and introns. Thus, a regulatory expression element group may be comprised, for instance, of a promoter operably linked 5' to a leader sequence. An EXP useful in practicing the present invention is presented as SEQ ID NO:1.

Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule function, such as a double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may be initially isolated from the 5' untranslated region (5' UTR) of a genomic copy of a gene. Alternately, promoters may be synthetically produced or manipulated DNA molecules. Promoters may also be chimeric. Chimeric promoters are produced through the fusion of two or more heterologous DNA molecules. A promoter that is useful in practicing the present invention includes promoter elements comprised within SEQ ID NO:2, or fragments or variants thereof. In specific embodiments of the invention, the claimed DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box, other known transcription factor binding site motif, or equivalent DNA sequence for recognition and binding of the RNA polymerase II complex for initiation of transcription.

In one embodiment, fragments of a promoter sequence disclosed herein are provided. Promoter fragments may comprise promoter activity, as described above, and may be useful alone or in combination with other promoters and promoter fragments, such as in constructing chimeric promoters, or in combination with other expression elements and expression element fragments. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having promoter activity as disclosed herein. In certain embodiments, provided herein are fragments of any one of SEQ ID NOs: 1-5 and 7, having the activity of the full length sequence. Methods for producing such fragments from a starting promoter molecule are well known in the art.

Compositions derived from any of the promoter elements comprised within SEQ ID NO:2 such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue- or cell-specific effects on expression. Compositions derived from any of the promoter elements comprised within SEQ ID NO:2 comprised of 3' deletions in which the TATA box element or equivalent sequence thereof and downstream sequence is removed can be used, for example, to make enhancer elements. Further deletions can be made to remove any elements that have positive or negative; tissue-specific; cell-specific; or timing-specific (such as, but not limited to, circadian rhythm) effects on expression. Any of the promoter elements comprised within SEQ ID NO:2 and fragments or enhancers derived therefrom can be used to make chimeric transcriptional regulatory element compositions.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, the term "leader" refers to a DNA molecule isolated from the untranslated 5' region (5' UTR) a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. Leaders useful in practicing the present invention are presented as SEQ ID NOs:3, or any of the leader elements comprised within SEQ ID NOs:3, or fragments or variants thereof. In specific embodiments, such DNA sequences may be defined as being capable of acting as a leader in a host cell, including, for example, a transgenic plant cell. In one embodiment, such sequences are decoded as comprising leader activity.

The leader sequences (also referred to as 5' UTRs) presented as SEQ ID NOs:3, or any of the leader elements comprised within SEQ ID NOs:3, may be comprised of regulatory elements, or may adopt secondary structures that can have an effect on transcription or translation of an operably linked transcribable DNA molecule. The leader sequence presented as SEQ ID NOs:3, or any of the leader elements comprised within SEQ ID NOs:3, can be used in accordance with the invention to make chimeric regulatory elements that affect transcription or translation of an operably linked transcribable DNA molecule.

As used herein, the term "intron" refers to a DNA molecule that may be isolated or identified from a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron.

In plants, the inclusion of some introns in gene constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from petunia (e.g., rbcS), potato (e.g., st-ls1), and from *Arabidopsis thaliana* (e.g., ubq3 and pat1). It has been shown that deletions or mutations within the splice sites of an intron reduce gene expression, indicating that splicing might be needed for IME. However, IME in dicotyledonous plants has been shown by point mutations within the splice sites of the pat1 gene from *A. thaliana*. Multiple uses of the same intron in one plant have been shown to exhibit disadvantages. In those cases, it is necessary to have a collection of basic control elements for the construction of appropriate recombinant DNA elements.

An intron useful in practicing the invention is presented as SEQ ID NO:4. Compositions derived from the intron presented as SEQ ID NO:4 can be comprised of internal deletions or duplications of cis regulatory elements. Further, alterations of the 5' and 3' sequences comprising the intron/exon splice junctions can be used to improve expression or specificity of expression when operably linked to a promoter+leader or chimeric promoter+leader and coding sequence. When modifying intron/exon boundary sequences, it may be beneficial to avoid using the nucleotide sequence AT or the nucleotide A just prior to the 5' end of the splice site (GT) and the nucleotide G or the nucleotide sequence TG just after the 3' end of the splice site (AG) to eliminate the potential of unwanted start codons from being formed during processing of the messenger RNA into the final transcript. The DNA sequence around the 5' or 3' end splice junction sites of the intron can be modified in this manner. Intron and intron variants altered as described herein and through methods known in the art can be tested empirically as described in the working examples to determine the intron's effect on expression of an operably linked DNA molecule. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

In one embodiment, fragments of an intron sequence disclosed herein are provided. Intron fragments may comprise the activity of the full length intron sequence, and may be useful alone or in combination with other introns or regulatory elements or expression element fragments. In specific embodiments, fragments of an intron are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having intron activity as disclosed herein. In certain embodiments, provided herein are fragments of SEQ ID NO: 4, having the activity of the full length sequence. Methods for producing such fragments from a starting intron molecule are well known in the art.

As used herein, the terms "3' transcription termination molecule," "3' untranslated region" or "3' UTR" refer to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region, wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and transported to the cytoplasm. Eukaryotic mRNAs are accumulated as poly(A) forms in vivo, making it difficult to detect transcriptional termination sites by conventional methods. Further, prediction of functional and efficient 3' UTRs by bioinformatics methods is difficult in that there are no conserved DNA sequences that would allow easy prediction of an effective 3' UTR.

From a practical standpoint, it is typically beneficial that a 3' UTR used in an expression cassette possesses the following characteristics. First, the 3' UTR should be able to efficiently and effectively terminate transcription of the transgene and prevent read-through of the transcript into any neighboring DNA sequence, which can be comprised of another expression cassette as in the case of multiple expression cassettes residing in one transfer DNA (T-DNA), or the neighboring chromosomal DNA into which the T-DNA has inserted. Second, the 3' UTR should not cause a reduction in the transcriptional activity imparted by the promoter, leader, enhancers, and introns that are used to drive expression of the DNA molecule. Finally, in plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette. An exemplary 3' UTR useful in practicing the invention is presented as SEQ ID NO:5.

In one embodiment, fragments of a 3' UTR disclosed herein are provided. 3' UTR fragments may comprise the activity of the full length 3' UTR sequence, and may be useful alone or in combination with other regulatory elements or expression element fragments. In specific embodiments, fragments of a 3' UTR are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having 3' UTR activity as disclosed herein. In certain embodiments, provided herein are fragments of SEQ ID NO: 5, having the activity of the full length sequence. Methods for producing such fragments from a starting 3' UTR molecule are well known in the art.

As used herein, the term "enhancer" or "enhancer element" refers to a cis-acting regulatory element, a.k.a. cis-element, which confers an aspect of the overall expression pattern, but is usually insufficient alone to drive transcription, of an operably linked transcribable DNA molecule. Unlike promoters, enhancer elements do not usually include a transcription start site (TSS), TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression. An example of an enhancer element derived from the *Bouteloua gracilis* putative ubiquitin gene promoter useful in practicing the invention is presented as SEQ ID NO:7.

Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter, DNA binding protein analysis using DNase I footprinting, methylation interference, electrophoresis mobility-shift assays, in vivo genomic footprinting by ligation-mediated polymerase chain reaction (PCR) and other conventional assays, or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods known in the art. Enhancer elements can be obtained by chemical synthesis or by isolation from regulatory elements that include such elements, and they can be synthesized with additional flanking nucleotides that contain useful restriction enzyme sites to facilitate subsequence manipulation. The design, construction, and use of enhancer elements for modulating the expression of operably linked transcribable DNA molecules are encompassed by the invention.

As used herein, the term "chimeric" refers to a single DNA molecule produced by fusing a first DNA molecule to a second DNA molecule, where neither the first nor the second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; for example, the fusion of a promoter to an enhancer element. The design, construction, and use of chimeric promoters for modulating the expression of operably linked transcribable DNA molecules are encompassed by the present invention.

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, the DNA sequences provided as SEQ ID NOs:1-5 or 7 may provide regulatory element reference sequences, wherein the constituent elements that comprise the reference sequence may be joined by methods known in the art and may comprise substitutions, deletions, and/or insertions of one or more nucleotides or mutations that naturally occur in bacterial and plant cell transformation.

As used herein, the term "variant" refers to a second DNA molecule, such as a regulatory element, that is in composition similar, but not identical to, a first DNA molecule, and wherein the second DNA molecule still maintains the general functionality, i.e. the same or similar expression pattern, for instance through more or less equivalent transcriptional activity, of the first DNA molecule. A variant may be a shorter or truncated version of the first DNA molecule or an altered version of the sequence of the first DNA molecule, such as one with different restriction enzyme sites or internal deletions, substitutions, or insertions. A "variant" can also encompass a regulatory element having a nucleotide sequence comprising a substitution, deletion, or insertion of one or more nucleotides of a reference sequence, wherein the derivative regulatory element has more or less or equivalent transcriptional or translational activity than the corresponding parent regulatory molecule. Regulatory element "variants" will also encompass variants arising from mutations that naturally occur in bacterial and plant cell transformation. In the present invention, the polynucleotide sequences provided as SEQ ID NOs:1-5 or 7 may be used to create variants that are in similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

The efficacy of the modifications, duplications, or deletions described herein on the desired expression aspects of a particular transgene may be tested empirically in stable and transient plant assays, such as those described in the working examples herein, so as to validate the results, which may vary depending upon the changes made and the goal of the change in the starting DNA molecule.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e. operably linked. As used herein, the term "vector" means any construct that may be used for the purpose of transformation, i.e., the introduction of heterologous DNA or RNA into a host cell. A construct typically includes one or more expression cassettes. As used herein, an "expression cassette" refers to a DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are so arranged that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter modulates transcription of the transcribable DNA molecule of interest in a cell. A leader, for example, is operably linked to DNA sequence when it is capable of affecting the transcription or translation of the DNA sequence.

The constructs of the invention may be provided, in one embodiment, as double tumor-inducing (Ti) plasmid border constructs that have the right border (RB or AGRtu.RB) and left border (LB or AGRtu.LB) regions of the Ti plasmid isolated from *Agrobacterium tumefaciens* comprising a T-DNA that, along with transfer molecules provided by the *A. tumefaciens* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower Mosaic Virus 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transgene encoding a non-chloroplast proteins.

Transcribable DNA molecules

As used herein, the term "transcribable DNA molecule" refers to any DNA molecule capable of being transcribed into a RNA molecule, including, but not limited to, those having protein coding sequences and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or genes that originate from, or are present in, the same species, but are incorporated into recipient cells by genetic engineering methods rather than classical breeding techniques.

A "transgene" refers to a transcribable DNA molecule heterologous to a host cell at least with respect to its location in the host cell genome or a transcribable DNA molecule artificially incorporated into a host cell's genome in the current or any prior generation of the cell.

A regulatory element, such as a promoter of the invention, may be operably linked to a transcribable DNA molecule that is heterologous with respect to the regulatory element. As used herein, the term "heterologous" refers to the combination of two or more DNA molecules when such a combination is not normally found in nature. For example, the two DNA molecules may be derived from different species or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs:1-5 or 7, operably linked to a heterologous transcribable DNA molecule so as to modulate transcription of the transcribable DNA molecule at a desired level or in a desired pattern when the construct is integrated in the genome of a transgenic plant cell. In one embodiment, the transcribable DNA molecule comprises a protein-coding region of a gene and in another embodiment the transcribable DNA molecule comprises an antisense region of a gene.

Genes of Agronomic Interest

A transcribable DNA molecule may be a gene of agronomic interest. As used herein, the term "gene of agronomic interest" refers to a transcribable DNA molecule that, when expressed in a particular plant tissue, cell, or cell type, confers a desirable characteristic. The product of a gene of agronomic interest may act within the plant in order to cause an effect upon the plant morphology, physiology, growth, development, yield, grain composition, nutritional profile, disease or pest resistance, environmental or chemical tolerance, or may act as a pesticidal agent in the diet of a pest that feeds on the plant. In one embodiment of the invention, a regulatory element of the invention is incorporated into a construct such that the regulatory element is operably linked to a transcribable DNA molecule that is a gene of agronomic interest. In a transgenic plant containing such a construct, the expression of the gene of agronomic interest can confer a beneficial agronomic trait. A beneficial agronomic trait may include, for example, but is not limited to, herbicide tolerance, insect control, modified yield, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, pharmaceutical peptides, improved processing qualities, improved flavor, hybrid seed production utility, improved fiber production, and desirable biofuel production.

Examples of genes of agronomic interest known in the art include those for herbicide resistance (e.g., U.S. Pat. Nos. 6,803,501; 6,448,476; 6,248,876; 6,225,114; 6,107,549; 5,866,775; 5,804,425; 5,633,435; and 5,463,175), increased yield (e.g., U.S. Pat. Nos. USRE38,446; 6,716,474; 6,663,906; 6,476,295; 6,441,277; 6,423,828; 6,399,330; 6,372,211; 6,235,971; 6,222,098; and 5,716,837), insect control (e.g., U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245; and 5,763,241), fungal disease resistance (e.g., U.S. Pat. Nos. 6,653,280; 6,573,361; 6,506,962; 6,316,407; 6,215,048; 5,516,671; 5,773,696; 6,121,436; 6,316,407; and 6,506,962), virus resistance (e.g., U.S. Pat. Nos. 6,617,496; 6,608,241; 6,015,940; 6,013,864; 5,850,023; and 5,304,730), nematode resistance (e.g., U.S. Pat. No. 6,228,992), bacterial disease resistance (e.g., U.S. Pat. No. 5,516,671), plant growth and development (e.g., U.S. Pat. Nos. 6,723,897 and 6,518,488), starch production (e.g., U.S. Pat. Nos. 6,538,181; 6,538,179; 6,538,178; 5,750,876; 6,476,295), modified oils production (e.g., U.S. Pat. Nos. 6,444,876; 6,426,447; and 6,380,462), high oil production (e.g., U.S. Pat. Nos. 6,495,739; 5,608,149; 6,483,008; and 6,476,295), modified fatty acid content (e.g., U.S. Pat. Nos. 6,828,475; 6,822,141; 6,770,465; 6,706,950; 6,660,849; 6,596,538; 6,589,767; 6,537,750; 6,489,461; and 6,459,018), high protein production (e.g., U.S. Pat. No. 6,380,466), fruit ripening (U.S. Pat. No. 5,512,466), enhanced animal and human nutrition (e.g., U.S. Pat. Nos. 6,723,837; 6,653,530; 6,541,259; 5,985,605; and 6,171,640), biopolymers (e.g., U.S. Pat. Nos. RE37,543; 6,228,623; and 5,958,745, and 6,946,588), environmental stress resistance (e.g., U.S. Pat. No. 6,072,103), pharmaceutical peptides and secretable peptides (e.g., U.S. Pat. Nos. 6,812,379; 6,774,283; 6,140,075; and 6,080,560), improved processing traits (e.g., U.S. Pat. No. 6,476,295), improved digestibility (e.g., U.S. Pat. No. 6,531,648) low raffinose (e.g., U.S. Pat. No. 6,166,292), industrial enzyme production (e.g., U.S. Pat. No. 5,543,576), improved flavor (e.g., U.S. Pat. No. 6,011,199), nitrogen fixation (e.g., U.S. Pat. No. 5,229,114), hybrid seed production (e.g., U.S. Pat. No. 5,689,041), fiber production (e.g., U.S. Pat. Nos. 6,576,818; 6,271,443; 5,981,834; and 5,869,720) and biofuel production (e.g., U.S. Pat. No. 5,998,700).

Alternatively, a gene of agronomic interest can affect the above mentioned plant characteristics or phenotypes by encoding a RNA molecule that causes the targeted modulation of gene expression of an endogenous gene, for example by antisense (see, e.g. U.S. Pat. No. 5,107,065); inhibitory RNA ("RNAi," including modulation of gene expression by miRNA-, siRNA-, trans-acting siRNA-, and phased sRNA-mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA molecule is transcribed into a molecule that is capable of causing gene suppression.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding β-glucuronidase (GUS), green fluorescent protein (GFP), proteins that confer antibiotic resistance, and proteins that confer herbicide tolerance. An example of a selectable marker transgene is provided as SEQ ID NO:6.

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also include progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a plant construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), gene editing (e.g., CRISPR-Cas systems), among others.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants of the invention, comprising the construct of this invention and expressing a gene of agronomic interest. Descriptions of breeding methods that are commonly used for different crops can be found in one of several reference books, see, e.g., Allard, *Principles of Plant Breeding*, John Wiley & Sons, NY, U. of CA, Davis, CA, 50-98 (1960); Simmonds, *Principles of Crop Improvement*, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses*, 2nd Edition, Monograph, 16:249 (1987); Fehr, *Principles of Variety Development, Theory and Technique*, (Vol. 1) and *Crop Species Soybean* (Vol. 2), Iowa State Univ., Macmillan Pub. Co., NY, 360-376 (1987).

The transformed plants may be analyzed for the presence of the gene or genes of interest and the expression level and profile conferred by the regulatory elements of the invention. Those of skill in the art are aware of the numerous methods available for the analysis of transformed plants. For example, methods for plant analysis include, but are not limited to, Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and non-regenerable. The invention also includes and provides transformed plant cells comprising a DNA molecule of the invention. The transformed or transgenic plant cells of the invention include regenerable and non-regenerable plant cells.

The invention also provides a commodity product that is produced from a transgenic plant or part thereof containing the recombinant DNA molecule of the invention. Commodity products of the invention contain a detectable amount of DNA comprising a DNA sequence selected from the group consisting of SEQ ID NOs:1-5 or 7. As used herein, a "commodity product" refers to any composition or product which is comprised of material derived from a transgenic plant, seed, plant cell, or plant part containing the recombinant DNA molecule of the invention. Commodity products include but are not limited to processed seeds, grains, plant parts, and meal. A commodity product of the invention will contain a detectable amount of DNA corresponding to the recombinant DNA molecule of the invention. Detection of one or more of this DNA in a sample may be used for determining the content or the source of the commodity product. Any standard method of detection for DNA molecules may be used, including methods of detection disclosed herein.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown is to be interpreted as illustrative and not in a limiting sense.

EXAMPLES

Example 1

Identification and Cloning of Regulatory Elements

Novel transcriptional regulatory elements and a regulatory expression element group (EXP) were identified and cloned from genomic DNA of the monocot species *Bouteloua gracilis*.

Using the identified sequences, a bioinformatic analysis was conducted to identify regulatory elements within the amplified DNA. For example, bioinformatics analysis was performed to identify the transcriptional start site (TSS) and any bi-directionality, introns, or upstream coding sequence present in the sequence. Using the results of this analysis, regulatory elements were defined within the DNA sequence and primers were designed to amplify the regulatory elements. The corresponding DNA molecules for the regulatory elements were amplified using standard polymerase chain reaction conditions with primers containing unique restriction enzyme sites and genomic DNA isolated from *Bouteloua gracilis*. The resulting DNA fragments were ligated into base plant expression vectors using standard restriction enzyme digestion of compatible restriction sites and DNA ligation methods.

Analysis of the regulatory element TSS and intron/exon splice junctions can be performed using transformed plant tissue. Briefly, the plants are transformed with the plant expression vectors comprising the cloned DNA fragments operably linked to a heterologous transcribable DNA molecule. Next, the 5' RACE System for Rapid Amplification of cDNA Ends, Version 2.0 (Invitrogen, Carlsbad, Calif. 92008) is used to confirm the regulatory element TSS and intron/exon splice junctions by analyzing the DNA sequence of the produced mRNA transcripts.

The DNA sequence encoding the *Bouteloua gracilis* transcriptional regulatory expression element group or EXP sequence derived from a putative Ubiquitin gene, which is comprised of a promoter element, operably linked to a leader element, operably linked to an intron element, is presented in Table 1, along with its corresponding promoter, leader, and intron. The 3' UTR corresponding to the *Bouteloua gracilis* putative Ubiquitin gene is also presented in Table 1.

TABLE 1

Transcriptional regulatory expression element group, promoter, leader, intron, and 3' UTR isolated from *Bouteloua gracilis*.

| Description | SEQ ID NO: | Description and/or regulatory elements of EXP linked in 5' → 3' direction (SEQ ID NOs): |
|---|---|---|
| EXP-BOUgr.Ubq: 2 | 1 | EXP: P-BOUgr.Ubq: 2 (SEQ ID NO: 2); L-BOUgr.Ubq: 1 (SEQ ID NO: 3); I-BOUgr.Ubq: 1 (SEQ ID NO: 4) |
| P-BOUgr.Ubq: 2 | 2 | Promoter |
| L-BOUgr.Ubq: 1 | 3 | Leader |
| I-BOUgr.Ubq: 1 | 4 | Intron |
| T-BOUgr.Ubq: 1 | 5 | 3' UTR |

Example 2

Analysis of Regulatory Elements Driving GUS Expression in Stably Transformed Corn Plants Corn plants were transformed with a vector, specifically a plant expression vector containing a test regulatory element driving expression of the β-glucuronidase (GUS) transgene. The resulting plants were analyzed for GUS protein expression, to assess the effect of the selected regulatory element on expression.

Corn plants were transformed with a plant GUS expression construct. The regulatory elements were cloned into a base plant expression vector using standard methods known in the art. The resulting plant expression vector contained a left border region from *Agrobacterium tumefaciens* (B-AGRtu.left border), a first transgene selection cassette used for selection of transformed plant cells that confers resistance to the herbicide glyphosate; a second transgene cassette to assess the activity of the regulatory element, which comprised EXP-BOUgr.Ubq:2 (SEQ ID NO:1) operably linked 5' to a synthetic coding sequence designed for expression in a plant cell encoding β-glucuronidase (GUS, GOI-Ec.uidA+St.LS1.nno:1, SEQ ID NO:6) containing a processable intron derived from the potato light-inducible tissue-specific ST-LS1 gene (Genbank Accession: X04753), operably linked 5' to a 3' termination region, T-BOUgr.Ubq:1 (SEQ ID NO:5); and a right border region from *Agrobacterium tumefaciens* (B-AGRtu.right border).

Corn plant cells were transformed using the binary transformation vector construct described above by *Agrobacterium*-mediated transformation, as is well known in the art. The resulting transformed plant cells were induced to form whole corn plants.

Histochemical GUS analysis was used for qualitative and quantitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues.

For quantitative analysis of GUS expression, total protein was extracted from selected tissues of transformed corn plants. One microgram of total protein was used with the fluorogenic substrate 4-methyleumbelliferyl-β-D-glucuronide (MUG) in a total reaction volume of 50 microliters. The reaction product, 4-methylumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 with Micromax Reader, with slit width set at excitation 2 nm and emission 3 nm. Values are provided in units of nmol GUS/hour/mg total protein.

The following tissues were sampled for GUS expression in the $R_0$ generation: V4 stage leaf and root; V7 stage leaf and root; VT stage flower/anther, leaf, and root; R1 stage Cob and silk; R3 stage 21 days after pollination (DAP) seed embryo and endosperm. Table 2 below shows the mean quantitative GUS expression for each of the sampled tissues driven by the regulatory element transgene cassette comprising EXP-BOUgr.Ubq:2 (SEQ ID NO:1) and T-BOUgr.Ubq:1 (SEQ ID NO:5).

TABLE 2

Mean quantitative GUS expression in stably transformed corn plants driven by regulatory elements derived from *Bouteloua gracilis*.

| Stage | Organ | Mean | Std Err |
|---|---|---|---|
| V4 | Leaf | 2552.55 | 895.34 |
| | Root | 6476.58 | 1383.15 |
| V7 | Leaf | 3622.05 | 1091.84 |
| | Root | 3953.61 | 1121.73 |
| VT | Flower, anthers | 9207.81 | 1587.9 |
| | Leaf | 8795.48 | 1795.25 |
| | Root | 4123.47 | 1207.1 |
| R1 | Cob, silk | 5994.73 | 1548.68 |
| R3 | Seed, 21DAP, Em | 10338.8 | 1592.33 |
| | Seed, 21DAP, En | 11249.6 | 746.08 |

As can be seen in Table 2, the highest level of expression imparted by the regulatory elements was observed in R3, 21 DAP seed embryos and endosperm. High expression was also observed in the VT stage flower, anthers, and leaf. Leaf expression appeared to increase in leaves from V4 to V7 stage. Root expression appeared to decline from V4 to V7 stage and then remained similar from V7 to VT stage.

Example 3

Enhancer Elements derived from the Regulatory Elements

Enhancers are derived from the promoter element presented as SEQ ID NO:2. The enhancer element may be comprised of one or more cis regulatory elements that when operably linked 5' or 3' to a promoter element, or operably linked 5' or 3' to additional enhancer elements that are operably linked to a promoter, can enhance or modulate expression levels of a transcribable DNA molecule, or provide expression of a transcribable DNA molecule in a specific cell type or plant organ or at a particular time point in development or circadian rhythm. Enhancers are made by removing the TATA box or functionally similar elements and any downstream sequence from the promoters that allow transcription to be initiated from the promoter presented as SEQ ID NO:2 or fragments thereof.

The TATA box in plant promoters is not as highly conserved as in some other eukaryotic organisms. Therefore, in order to define a fragment as an enhancer, one first must identify the transcriptional start site (TSS) of the gene, wherein the 5' UTR is first transcribed. For example, the transcriptional regulatory element, EXP-BOUgr.Ubq:2 (SEQ ID NO:1) is comprised of the promoter element, P-BOUgr.Ubq:2 (SEQ ID NO:2), operably linked to the 5' UTR or leader element, L-BOUgr.Ubq:1 (SEQ ID NO:3), which is operably linked to the intron element, I-BOUgr.Ubq:1 (SEQ ID NO:4). Within the 1095 bp promoter element, P-BOUgr.Ubq:2 (SEQ ID NO:2), the putative core TATA-like element is found within nucleotides 1046 through 1053. An enhancer fragment derived from the P-BOUgr.Ubq:2 could comprise nucleotides 1 through 1045 of SEQ ID NO:2, resulting in the sequence presented as SEQ ID NO:7 (E-BOUgr.Ubq). Enhancers derived from the promoter, P-BOUgr.Ubq:2 (SEQ ID NO:2), can further comprise smaller fragments of E-BOUgr.Ubq (SEQ ID NO:7). The effectiveness of the enhancer elements derived from the promoter, P-BOUgr.Ubq:2 is empirically determined by building a chimeric transcriptional regulatory element comprising an enhancer derived from the promoter, P-BOUgr.Ubq:2, which is operably linked to a promoter and leader and used to drive expression of a transcribable DNA molecule such as GUS in stable or transient plant assay.

Further refinement of the enhancer element may be required and is validated empirically. In addition, position of the enhancer element relative to other elements within a chimeric transcriptional regulatory element is also empirically determined, since the order of each element within the chimeric transcriptional regulatory element may impart different effects, depending upon the relative positions of each element. Some promoter elements will have multiple TATA box or TATA box-like elements and potentially multiple transcription start sites. Under those circumstances, it may be necessary to first identify where the first TSS is located and then begin designing enhancers using the first TSS to prevent the potential initiation of transcription from occurring within a putative enhancer element.

Enhancer elements, derived from the promoter element presented as SEQ ID NO:2 are cloned using methods known in the art to be operably linked 5' or 3' to a promoter element, or operably linked 5' or 3' to additional enhancer elements that are operably linked to a promoter. Alternatively, enhancer elements can be cloned, using methods known in the art, to provide a larger enhancer element that is comprised of two or more copies of the enhancer and cloned using methods known in the art to be operably linked 5' or 3' to a promoter element, or operably linked 5' or 3' to additional enhancer elements that are operably linked to a promoter producing a chimeric transcriptional regulatory element. Enhancer elements can also be cloned using methods known in the art to be operably linked 5' to a promoter element derived from a different genus organism, or operably linked 5' or 3' to additional enhancer elements derived from other genus organisms that are operably linked to a promoter derived from either the same or different genus organism, resulting in a chimeric transcriptional regulatory element. A GUS expression plant transformation vector may be constructed using methods known in the art similar to the construct described in Example 2 in which the resulting plant expression vectors contain a left border region from Agrobacterium tumefaciens (B-AGRtu.left border), a first transgene selection cassette used for selection of transformed plant cells that confers resistance to the herbicide glyphosate; and a second transgene cassette to test the enhancer element comprised of the enhancer element operably linked 5' or 3' to a promoter element or operably linked 5' or 3' to additional enhancer elements that are in turn operably linked to a promoter which is operably linked 5' to a leader element, operably linked 5' to an intron element, operably linked to a coding sequence for β-glucuronidase (GOI-Ec.uidA+St.LS1.nno:1, SEQ ID NO:6) containing a processable intron derived from the potato light-inducible tissue-specific ST-LS1 gene (Genbank Accession: X04753), operably linked to a 3' termination region from the Oryza sativa Lipid Transfer Protein-like gene (T-Os.LTP:1, SEQ ID NO:8); and a right border region from A. tumefaciens (B-AGRtu.right border). The resulting plasmids are used to transform corn plants or other monocot genus plants by the methods described above. Alternatively, protoplast cells derived from corn or other monocot genus plants are transformed using methods known in the art to perform transient assays GUS expression driven by a regulatory element comprising one or more enhancers is evaluated in stable or transient plant assays to determine the effects of the enhancer element on expression of a transcribable DNA molecule. Modifications to one or more enhancer elements or duplication of one or more enhancer elements may be performed based upon empirical experimentation and the resulting gene expression regulation that is observed using each regulatory element composition. Altering the relative positions of one or more enhancers in the resulting regulatory or chimeric regulatory elements may affect the transcriptional activity or specificity of the regulatory or chimeric regulatory element and is determined empirically to identify the best enhancers for the desired transgene expression profile within the corn plant or other genus plant.

Example 4

Analysis of Intron Enhancement of GUS Activity Using Plant Derived Protoplasts

An intron is selected based upon experimentation and comparison with an intronless expression vector control to empirically select an intron and configuration within the vector transfer DNA (T-DNA) element arrangement for optimal expression of a transgene. For example, in the expression of an herbicide resistance gene, such as CP4, which confers tolerance to glyphosate, it is desirable to have transgene expression within the reproductive tissues as well as the vegetative tissues, to prevent the loss of yield when applying the herbicide. An intron in this instance would be selected upon its ability, when operably linked to a constitutive promoter, to enhance expression of the herbicide resistance conferring transgene, particularly within the reproductive cells and tissues of the transgenic plant, thus providing both vegetative and reproductive tolerance to the transgenic plant when sprayed with the herbicide. In most ubiquitin genes, the 5' UTR is comprised of a leader, which has an intron sequence embedded within it. The regulatory elements derived from such genes are therefore assayed using the entire 5' UTR comprising the promoter, leader, and intron. To achieve different expression profiles or to modulate the level of transgene expression, the intron from such a regulatory element may be removed or substituted with a heterologous intron.

The intron I-BOUgr.Ubq:1, presented herein as SEQ ID NO:4, is identified using genomic DNA contigs in comparison to expressed sequence tag clusters or cDNA contigs to identify exon and intron sequences within the genomic DNA. In addition, 5' UTR or leader sequence is also used to define the intron/exon splice junction of one or more introns under conditions when the gene sequence encodes a leader sequence that is interrupted by one or more introns. Introns are cloned using methods known in the art into a plant transformation vector to be operably linked 3' to a regulatory element and leader fragment and operably linked 5' to either a second leader fragment or to coding sequences.

As discussed above, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The DNA sequence around the 5' or 3' end splice junction sites of the intron can thus be modified.

The introns are assayed for an enhancement effect through the ability to enhance expression in transformed stable plant assay. For transient assay of intron enhancement, a base plant vector is constructed using methods known in the art. The intron is cloned into a base plant vector similar to that described in Example 2 which comprises an expression cassette comprised of a constitutive promoter such as the enhanced Cauliflower mosaic virus promoter and leader, P+L-CaMV.35S-enh (SEQ ID NO:9), operably linked 5' to a test intron element (e.g., SEQ ID NO:4), operably linked to a coding sequence for GUS that possesses a processable intron (GOI-Ec.uidA+St.LS1.nno:1, SEQ ID NO:6), operably linked to the Nopaline synthase 3' UTR from A. tumefaciens (T-AGRtu.nos-1:1:13, SEQ ID NO:10); and a second expression cassette for selection of the transformed plant cells. Corn plant cells are transformed using the binary transformation vector construct described above by Agrobacterium-mediated transformation, as is well known in the art. The resulting transformed plant cells were induced to form whole corn plants. Single-copy or low copy number transformants are selected for comparison to single-copy or low copy number transformed plants, transformed with a plant transformation vector identical to the test vector but without the test intron to determine if the test intron provides an intron mediated enhancement effect.

The intron I-BOUgr.Ubq:1, presented herein as SEQ ID NO:4, can be modified in a number of ways, such as deleting fragments within the intron sequence, which may reduce expression or duplication of fragments with the intron that may enhance expression. In addition, DNA sequences within the intron that may affect the specificity of expression to either particular cells types or tissues and organs can be duplicated or altered or deleted to affect expression and patterns of expression of the transgene. In addition, the intron provided herein can be modified to remove any potential start codons (ATG) that may cause unintentional transcripts from being expressed from improperly spliced introns as different, longer or truncated proteins. Once the intron has been empirically tested, or it has been altered based upon experimentation, the intron is used to enhance expression of a transgene in stably transformed plants that can be of any genus monocot or dicot plant, so long as the intron provides enhancement of the transgene. The intron can also be used to enhance expression in other organisms, such as algae, fungi, or animal cells, so long as the intron provides enhancement or attenuation or specificity of expression of the transgene to which it is operably linked.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a polynucleotide selected from the group consisting of:
   a) a polynucleotide with at least 95 percent sequence identity to SEQ ID NO: 2, wherein the polynucleotide has promoter activity;
   b) a polynucleotide with at least 97 percent sequence identity to any of SEQ ID NOs: 1, 3-5 or 7, wherein the polynucleotide has gene-regulatory activity;
   c) a polynucleotide comprising any of SEQ ID NOs:1-5 or 7; and
   d) a fragment comprising at least 150 contiguous nucleotides of SEQ ID NO: 2, wherein the fragment has promoter activity;
   wherein said polynucleotide is operably linked to a heterologous transcribable DNA molecule.

2. The recombinant DNA molecule of claim 1, wherein said polynucleotide has at least 97 percent sequence identity to SEQ ID NO:2.

3. The recombinant DNA molecule of claim 1, wherein said polynucleotide has at least 99 percent sequence identity to the DNA sequence of any of SEQ ID NOs: 1-5 or 7.

4. The recombinant DNA molecule of claim 1, wherein said polynucleotide comprises any of SEQ ID NOs: 1-5 or 7.

5. The recombinant DNA molecule of claim 1, wherein the heterologous transcribable DNA molecule comprises a gene of agronomic interest.

6. The recombinant DNA molecule of claim 5, wherein the gene of agronomic interest confers herbicide tolerance in plants.

7. The recombinant DNA molecule of claim 5, wherein the gene of agronomic interest confers pest resistance in plants.

8. A transgenic plant cell comprising a recombinant DNA molecule comprising a polynucleotide selected from the group consisting of:

a) a polynucleotide with at least 95 percent sequence identity to SEQ ID NO: 2, wherein the polynucleotide has promoter activity;
b) a polynucleotide with at least 97 percent sequence identity to any of SEQ ID NOs: 1, 3-5 or 7, wherein the polynucleotide has gene-regulatory activity;
c) a polynucleotide comprising any of SEQ ID NOs:1-5 or 7; and
d) a fragment comprising at least 150 contiguous nucleotides of SEQ ID NO: 2, wherein the fragment has promoter activity;
wherein said polynucleotide is operably linked to a heterologous transcribable DNA molecule.

9. The transgenic plant cell of claim 8, wherein said transgenic plant cell is a monocotyledonous plant cell.

10. The transgenic plant cell of claim 8, wherein said transgenic plant cell is a dicotyledonous plant cell.

11. A transgenic plant, or part thereof, comprising the recombinant DNA molecule of claim 1.

12. A progeny plant of the transgenic plant of claim 11, or a part thereof, wherein the progeny plant or part thereof comprises said recombinant DNA molecule.

13. A transgenic seed, wherein the seed comprises the recombinant DNA molecule of claim 1.

14. A method of producing a commodity product comprising obtaining a transgenic plant or part thereof according to claim 11 and producing the commodity product therefrom.

15. The method of claim 14, wherein the commodity product is protein concentrate, protein isolate, grain, starch, seeds, meal, flour, biomass, or seed oil.

16. A method of expressing a transcribable DNA molecule comprising obtaining a transgenic plant according to claim 11 and cultivating plant, wherein the transcribable DNA is expressed.

17. A method of producing a transgenic plant cell comprising introducing the recombinant DNA molecule of claim 1 into a plant cell.

18. The method of claim 17, wherein introducing said recombinant DNA molecule into said plant cell comprises transformation.

19. The method of claim 18, further comprising regenerating a transgenic plant from said plant cell.

20. The method of claim 17, wherein introducing said recombinant DNA molecule into said plant cell comprises crossing the transgenic plant of claim 11 with another plant to produce a progeny plant comprising said plant cell.

* * * * *

SEQUENCE LISTING

```
<160> NUMBER OF SEQ ID NOS: 10

<210> SEQ ID NO 1
<211> LENGTH: 2066
<212> TYPE: DNA
<213> ORGANISM: Bouteloua gracilis
<220> FEATURE:
<221> NAME/KEY: misc_feature
<222> LOCATION: (1)..(2066)
<223> OTHER INFORMATION: DNA sequence of a regulatory expression element
      group comprising a promoter, leader, and intron operably linked
      and derived from a putative ubiquitin gene from Blue Gama grass.

<400> SEQUENCE: 1
tacgagcaaa cgcacaaccg ggatacagat ctacggtaca gaggttactt ccaacgggaa      60
ggttcccgtc cctctagcgc aagcaagacg acgcagagat ggtgaccaaa aacgattctt     120
tgctttacct ggtcatgaca ccaccggata cggataagaa ggaaaaccgg agcatctcta     180
gcaatagaga aatcgacgtt gcctcctaga ggaagaaagc gacggcctat gcttttttct     240
tttgtcgatg attccactga attgtttctc tattttttc gttgtgtaat ggtcctggta      300
caaacgttca tccaatcatg caacttgcaa gaataaaaat aaaaaatata atctcagacg     360
tccaatcatg gcttcctaaa aaaataaaaa ggacgagaaa ctactcagaa aaaataaata     420
aatacacaac tgtaggaacc aaagcaaagt tgacaaggaa ccaaagcaag gcaggtccac     480
atgtgctgcg agcaggtgcg cctcctcctc cgtttcttcg ccttgctaat cacgtcgcta     540
aatacagagg ccgacttaag aatgccgaca tggcaatttt gctggatatt tttgcttcct     600
tgtagtatca aacagaagaa tattaacgtg ggagtataca gtaattttct tttaccattt     660
ttctttaatc gcgttttgt tcaaccaaac acaactttag acgtactagt actccactat      720
ttttattttt attttctcct acagtacttt tgaaaaaaag gaatcttgtc atgcatgatt     780
gagatcacgg taacgcgac tcacgccgcc gcacgggtaa cggccaccaa ccaaaagtag      840
caaacggcgt caacctcctc gacatctccg cgtcgctttt cttttctcc gcagagaatg      900 agtggcgggg agggacccca cgacgcaacc ccacgacgca accgcttatc gcagccgggt     960
ccacaccgca ccgctgccgt agcgtcatgg gactcggccc gcggccgcc ctccgacccg     1020 gaccgcttt ccttccccte ccgtgtataa ataccgcccc cctgctcgc ctcctcccca     1080 atccatccga tccccaatcc agtcccgcga gcgaaatcgc cgacgaccga tcgaagcgaa    1140
gcagccttcc cccatcctct caaggtatgc gaattctcga tcctcctctc ctatgttcgt    1200
tgtggatctg ctggttagga ttgattaggt tgtcgtacca tgccttttc ctgttcgtgt    1260 tcctcagatc tatagtcggt ttgcacaggt agagggctaa tctctagtcg atctgcgggt    1320
agagttgttg aatcatgtgc tgccttcagt tcatgtggtt tagatccgtg ttgcttgttg    1380
cggtcatgtg ttcacacaac acgtacggtt cctgccgtgc gcggattagc cgcgctgagg    1440
ctctgacgtt gtcggtgtgg gcgtgatcgc gcgggctgcc taggcttgtt attgttgaat    1500
taggcttggt cgattgggtc tgtttctatt cacggatggt cttcgatggt tcatgtgcat    1560
gctgttggtc gctggttagg tggtgatacc gttcgatttt tgtttaatct gtctagaatt    1620
ccttagatct gaaattctgt gatgtctaca tccagctgct tgttgttgaa tatttagct    1680
```

```
atgttaatct gccatggtct tcgtagtttc catgcataaa gccatgcaaa tacgttgtat      1740
atttactgtt gctgcaaccc atctcagatt ctagtttgct gtgtactatt aggccttgta      1800
aatgcttgtt aaaatggtta taaattgtgt tcatggttct gtgcctgtta agtcgtcatg      1860
tttatttcct ggctgatgct atctgtgggt agaatttgca taggcttcaa tctactgact      1920
ctatgggtag gatctgtgta gcgttgcatc aaacatggca gtgtcttaat gctttcacat      1980
aaaatgtgga actgtttata ttattattat gtactgcatg ttttggtggc ctaactttgc      2040
ctctgctgct aaatttgcag gtgcag                                           2066
```

<210> SEQ ID NO 2
<211> LENGTH: 1095
<212> TYPE: DNA
<213> ORGANISM: Bouteloua gracilis
<220> FEATURE:
<221> NAME/KEY: misc_feature
<222> LOCATION: (1)..(1095)
<223> OTHER INFORMATION: Promoter sequence derived from a putative
      ubiquitin gene from Blue Gama grass.

<400> SEQUENCE: 2

```
tacgagcaaa cgcacaaccg ggatacagat ctacggtaca gaggttactt ccaacgggaa        60
ggttcccgtc cctctagcgc aagcaagacg acgcagagat ggtgaccaaa aacgattctt       120
tgctttacct ggtcatgaca ccaccggata cggataagaa ggaaaaccgg agcatctcta       180
gcaatagaga aatcgacgtt gcctcctaga ggaagaaagc gacggcctat gcttttttct       240
tttgtcgatg attccactga attgtttctc tattttttc gttgtgtaat ggtcctggta        300
caaacgttca tccaatcatg caacttgcaa gaataaaaat aaaaaatata atctcagacg       360
tccaatcatg gcttcctaaa aaataaaaa ggacgagaaa ctactcagaa aaataaata         420 aatacacaac tgtaggaacc aaagcaaagt tgacaaggaa ccaaagcaag gcaggtccac       480
atgtgctgcg agcaggtgcg cctcctcctc cgtttcttcg ccttgctaat cacgtcgcta       540
aatacagagg ccgacttaag aatgccgaca tggcaatttt gctggatatt tttgcttcct      600
tgtagtatca aacagaagaa tattaacgtg ggagtataca gtaattttct tttaccattt       660
ttctttaatc gcgttttgt tcaaccaaac acaactttag acgtactagt actccactat        720
tttttatttt attttctcct acagtacttt tgaaaaaag gaatcttgtc atgcatgatt        780
gagatcacgg taacggcgac tcacgccgcc gcacgggtaa cggccaccaa ccaaaagtag       840
caaacggcgt caacctcctc gacatctccg cgtcgctttt cttttttctcc gcagagaatg     900 agtggcgggg agggacccca cgacgcaacc ccacgacgca accgcttatc gcagccgggt      960
ccacaccgca ccgctgccgt agcgtcatgg gactcggccc gcggcccgcc ctccgacccg     1020
gacccgcttt ccttcccctc ccgtgtataa ataccgcccc cctgctcgc ctcctcccca      1080 atccatccga tcccc                                                     1095
```

<210> SEQ ID NO 3
<211> LENGTH: 69
<212> TYPE: DNA
<213> ORGANISM: Bouteloua gracilis
<220> FEATURE:
<221> NAME/KEY: misc_feature
<222> LOCATION: (1)..(69)
<223> OTHER INFORMATION: Leader sequence derived from a putative
      ubiquitin gene from Blue Gama grass.

<400> SEQUENCE: 3

```
aatccagtcc cgcgagcgaa atcgccgacg accgatcgaa gcgaagcagc cttcccccat    60
cctctcaag                                                            69
```

<210> SEQ ID NO 4
<211> LENGTH: 902
<212> TYPE: DNA
<213> ORGANISM: Bouteloua gracilis
<220> FEATURE:
<221> NAME/KEY: misc_feature
<222> LOCATION: (1)..(902)
<223> OTHER INFORMATION: Intron sequence derived from a putative
      ubiquitin gene from Blue Gama grass.

<400> SEQUENCE: 4

```
gtatgcgaat tctcgatcct cctctcctat gttcgttgtg gatctgctgg ttaggattga    60
ttaggttgtc gtaccatgcc ttttcctgt tcgtgttcct cagatctata gtcggtttgc    120
acaggtagag ggctaatctc tagtcgatct gcgggtagag ttgttgaatc atgtgctgcc    180
ttcagttcat gtggtttaga tccgtgttgc ttgttgcggt catgtgttca cacaacacgt    240
acggttcctg ccgtgcgcgg attagccgcg ctgaggctct gacgttgtcg gtgtgggcgt    300
gatcgcgcgg gctgcctagg cttgttattg ttgaattagg cttggtcgat tgggtctgtt    360
tctattcacg gatggtcttc gatggttcat gtgcatgctg ttggtcgctg gttaggtggt    420
gataccgttc gattttgtt taatctgtct agaattcctt agatctgaaa ttctgtgatg    480
tctacatcca gctgcttgtt gttgaatatt ttagctatgt taatctgcca tggtcttcgt    540
agtttccatg cataaagcca tgcaaatacg ttgtatattt actgttgctg caacccatct    600
cagattctag tttgctgtgt actattaggc cttgtaaatg cttgttaaaa tggttataaa    660
ttgtgttcat ggttctgtgc ctgttaagtc gtcatgttta ttttctggct gatgctatct    720
gtgggtagaa tttgcatagg cttcaatcta ctgactctat gggtaggatc tgtgtagcgt    780
tgcatcaaac atggcagtgt cttaatgctt tcacataaaa tgtggaactg tttatattat    840
tattatgtac tgcatgtttt ggtggcctaa ctttgcctct gctgctaaat ttgcaggtgc    900
ag                                                                   902
```

<210> SEQ ID NO 5
<211> LENGTH: 498
<212> TYPE: DNA
<213> ORGANISM: Bouteloua gracilis
<220> FEATURE:
<221> NAME/KEY: misc_feature
<222> LOCATION: (1)..(498)
<223> OTHER INFORMATION: 3' untranslated region derived from a putative
      ubiquitin gene from Blue Gama grass.

<400> SEQUENCE: 5

```
gtttggtcag gagctgctct tgtctctggt ttcacaagta tggtgtctct ggtgtatggc    60
gtgtccagtc ccgttgtggt tcgactgatg tctctgtcgt gttatgagtc ctatgtcgtc    120
tggttgtccg tgtgaaacat tgctgcatgt gcagctaatt cgtgtgaaac attgctgcat    180
gtgcagctgg ttggtttatg aataagtgaa acctgaactt tgtgtgaatt ctgcttcctc    240
tatgcgctga atgttttgat tgtgatcttt tatctactca cagttgctga gatgataagg    300
ctgaatcaat gtagagctaa gattctctcg taaatgttta tattaaatac cttgtgtaat    360
tgcgagtaca aatcgacagt aattcaagct gcggttcttt gttcatccag aaggccaaga    420
```

```
ttgcaaattc aggtttcttg gcagtgaaag attgaacgca tgcaaatttc ctttgttctt      480
ttgatcacaa aattgatc                                                     498

<210> SEQ ID NO 6
<211> LENGTH: 2001
<212> TYPE: DNA
<213> ORGANISM: Artificial
<220> FEATURE:
<223> OTHER INFORMATION: Synthetic coding sequence encoding Beta-
      glucuronidase designed for expression in a plant cell.

<400> SEQUENCE: 6
atggtgaggc cgttgagac cccgactagg gagatcaaga agctggacgg cctctgggcc         60
ttctccctcg accgtgagaa ctgcggcatc gaccagcgct ggtgggagtc cgccctccag       120
gagtctaggg ccatcgccgt gcccggttcc ttcaacgacc agttcgccga cgccgacatc       180
cgcaactacg cgggcaacgt ctggtatcag cgcgaggtgt tcatcccgaa gggctgggcg       240
ggccagcgca tcgtgctccg cttcgacgcc gtgacccact acggcaaggt ctgggtgaac       300
aatcaggagg taagtttctg cttctacctt tgatatatat ataataatta tcattaatta       360
gtagtaatat aatatttcaa atatttttt caaaataaaa gaatgtagta tatagcaatt       420
gcttttctgt agtttataag tgtgtatatt ttaatttata acttttctaa tatatgacca       480
aaatttgttg atgtgcaggt gatggagcac cagggcggtt acaccccgtt cgaggccgac       540
gtgacgccgt acgtgatcgc cgggaagtcc gtccgcatca ccgtctgcgt gaacaatgag       600
ctgaactggc agaccatccc gcctggcatg gtcataccg acgagaacgg caagaagaag       660
cagtcctact ccacgactt cttcaactac gctggcatcc accgctccgt gatgctctac       720
accactccca cacctgggt ggacgacatc ccgtggtca cccacgtggc ccaggactgc       780
aaccacgcct ccgtggactg gcaagtcgtt gccaacggcg acgtcagcgt cgagctgcgc       840
gacgccgacc agcaagtcgt tgccaccggc cagggcacca gcggcaccct ccaagtcgtc       900
aaccctcacc tctggcagcc tggcgagggc tacctctacg agctgtgcgt caccgccaag       960
agccagactg agtgcgacat ctaccctctc cgcgtcggca tcaggagcgt cgctgtcaag      1020
ggcgagcagt tcctcatcaa ccacaagcct ttctacttca ctggtttcgg ccgccacgag      1080
gacgctgacc tgagggcaa gggtttcgac aacgtcctga tggtccacga ccacgctctg      1140
atggactgga tcggtgccaa cagctacagg accagtcact acccgtacgc tgaggagatg      1200
ctggactggg ctgacgagca cggtatcgtc gtgatcgacg agactgctgc ggtcggtttc      1260
aacctgtctc tgggcattgg tttcgaggct gggaacaagc cgaaggagct gtactctgag      1320
gaagctgtca acggcgagac tcagcaagct catctccagg cgattaagga gctgattgcc      1380
agggacaaga accatccgtc tgtcgtgatg tggtctattg caatgagcc ggacaccaga      1440 ccgcaagggg cgcgtgaata cttcgcgccg ctggcggagg cgactcgcaa actggaccca      1500
acccgtccaa tcacgtgcgt caatgtcatg ttctgcgacg cccatacgga tacgatctcg      1560
gacctgttcg atgttctttg tctcaatcgg tactatgggt ggtatgttca gagcggggat      1620
cttgagacgg cggagaaggt tcttgagaag gaactcctgg cgtggcaaga gaagctccat      1680
cagccgatca ttatcacgga gtacgggttt gacacacttg cgggccttca cagtatgtac      1740
acagatatgt ggtcggagga ataccagtgt gcatggttgg atatgtacca tcgtgtcttc      1800 gacccgggttt cagcggttgt cggcgaacaa gtctggaact tcgcagactt cgccacgagc      1860
caagggatac tgcgggtagg agggaacaag aagggaatct tcacacggga tcggaagccc      1920
```

```
aagtcagcag ccttcctgtt gcagaagcga tggacaggaa tgaacttcgg agaaaagcca    1980
cagcaaggcg gaaagcagtg a                                              2001
```

<210> SEQ ID NO 7
<211> LENGTH: 1045
<212> TYPE: DNA
<213> ORGANISM: Bouteloua gracilis
<220> FEATURE:
<221> NAME/KEY: misc_feature
<222> LOCATION: (1)..(1045)
<223> OTHER INFORMATION: Enhancer derived from the promoter of a
      putative ubiquitin gene from Blue Gama grass.

<400> SEQUENCE: 7

```
tacgagcaaa cgcacaaccg ggatacagat ctacggtaca gaggttactt ccaacgggaa      60
ggttcccgtc cctctagcgc aagcaagacg acgcagagat ggtgaccaaa aacgattctt     120
tgctttacct ggtcatgaca ccaccggata cggataagaa ggaaaaccgg agcatctcta     180
gcaatagaga aatcgacgtt gcctcctaga ggaagaaagc gacggcctat gcttttttct     240
tttgtcgatg attccactga attgtttctc tattttttc gttgtgtaat ggtcctggta      300
caaacgttca tccaatcatg caacttgcaa gaataaaaat aaaaaatata atctcagacg     360
tccaatcatg gcttcctaaa aaaataaaaa ggacgagaaa ctactcagaa aaaataaata     420
aatacacaac tgtaggaacc aaagcaaagt tgacaaggaa ccaaagcaag gcaggtccac     480
atgtgctgcg agcaggtgcg cctcctcctc cgtttcttcg ccttgctaat cacgtcgcta     540
aatacagagg ccgacttaag aatgccgaca tggcaatttt gctggatatt tttgcttcct    600
tgtagtatca aacagaagaa tattaacgtg ggagtataca gtaattttct tttaccattt     660
ttctttaatc gcgttttgt tcaaccaaac acaactttag acgtactagt actccactat      720
tttttatttt attttctcct acagtacttt tgaaaaaaag gaatcttgtc atgcatgatt     780
gagatcacgg taacggcgac tcacgccgcc gcacgggtaa cggccaccaa ccaaaagtag     840
caaacggcgt caacctcctc gacatctccg cgtcgctttt cttttctcc gcagagaatg      900 agtggcgggg agggacccca cgacgcaacc ccacgacgca accgcttatc gcagccgggt     960
ccacaccgca ccgctgccgt agcgtcatgg gactcggccc gcggcccgcc ctccgacccg    1020
gacccgcttt ccttcccctc ccgtg                                          1045
```

<210> SEQ ID NO 8
<211> LENGTH: 300
<212> TYPE: DNA
<213> ORGANISM: Oryza sativa
<220> FEATURE:
<221> NAME/KEY: misc_feature
<222> LOCATION: (1)..(300)
<223> OTHER INFORMATION: 3' untranslated region derived from a rice
      Lipid Transfer Protein-like gene.

<400> SEQUENCE: 8

```
attaatcgat cctccgatcc cttaattacc ataccattac accatgcatc aatatccata     60
tatatataaa cccttttcgca cgtacttata ctatgttttg tcatacatat atatgtgtcg    120
aacgatcgat ctatcactga tatgatatga ttgatccatc agcctgatct ctgtatcttg    180
ttatttgtat accgtcaaat aaaagttcct tccacttgtg ttaataatta gctactctca    240
tctcatgaac cctatatata actagtttaa tttgctgtca attgaacatg atgatcgatg    300
```

```
<210> SEQ ID NO 9
<211> LENGTH: 631
<212> TYPE: DNA
<213> ORGANISM: Artificial
<220> FEATURE:
<223> OTHER INFORMATION: An enhanced promoter and native leader sequence
      derived from the Cauliflower mosaic virus.

<400> SEQUENCE: 9
ggtccgatgt gagactttc aacaaagggt aatatccgga aacctcctcg gattccattg      60
cccagctatc tgtcacttta ttgtgaagat agtggaaaag gaaggtggct cctacaaatg     120
ccatcattgc gataaaggaa aggccatcgt tgaagatgcc tctgccgaca gtggtcccaa     180
agatggaccc ccacccacga ggagcatcgt ggaaaaagaa gacgttccaa ccacgtcttc     240
aaagcaagtg gattgatgtg atggtccgat gtgagacttt tcaacaaagg gtaatatccg     300
gaaacctcct cggattccat tgcccagcta tctgtcactt tattgtgaag atagtggaaa     360
aggaaggtgg ctcctacaaa tgccatcatt gcgataaagg aaaggccatc gttgaagatg     420
cctctgccga cagtggtccc aaagatggac ccccacccac gaggagcatc gtggaaaaag     480
aagacgttcc aaccacgtct tcaaagcaag tggattgatg tgatatctcc actgacgtaa     540
gggatgacgc acaatcccac tatccttcgc aagacccttc ctctatataa ggaagttcat     600
ttcatttgga gaggacacgc tgaacacgct g                                    631

<210> SEQ ID NO 10
<211> LENGTH: 253
<212> TYPE: DNA
<213> ORGANISM: Agrobacterium tumefaciens
<220> FEATURE:
<221> NAME/KEY: misc_feature
<222> LOCATION: (1)..(253)
<223> OTHER INFORMATION: 3' untranslated region derived from the
      nopaline synthase gene of Agrobacterium tumefaciens.

<400> SEQUENCE: 10
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg gttttttatg attagagtcc cgcaattata catttaatac     180
gcgatagaaa acaaaatata gcgcgcaaac taggataaat tatcgcgcgc ggtgtcatct     240
atgttactag atc                                                        253
```